United States Patent [19]

Simon et al.

[11] 3,968,801

[45] July 13, 1976

[54] CALF PULLER

[76] Inventors: Jerry Lee Simon, Zeona, S. Dak. 57795; Larry Ray Schuelke, Mud Butte, S. Dak. 57758

[22] Filed: Nov. 14, 1974

[21] Appl. No.: 523,672

[52] U.S. Cl. .................. 128/352; 254/108

[51] Int. Cl.[2] .................. A61B 17/42

[58] Field of Search .......... 128/323, 324, 352, 353, 128/361; 254/108–112, 131, 132

[56] References Cited

UNITED STATES PATENTS

| | | | |
|---|---|---|---|
| 894 | 8/1838 | Kilburn | 254/108 |
| 130,449 | 8/1872 | Stuart | 254/108 |
| 359,405 | 3/1887 | Scott | 254/108 |
| 470,116 | 3/1892 | Finsterer | 254/108 |
| 652,550 | 6/1900 | Robinson | 254/108 |
| 945,334 | 1/1910 | Lent | 254/108 |

FOREIGN PATENTS OR APPLICATIONS

| | | | |
|---|---|---|---|
| 484,955 | 9/1953 | Italy | 128/361 |
| 132,207 | 9/1900 | United Kingdom | 128/324 |

*Primary Examiner*—Lawrence W. Trapp
*Attorney, Agent, or Firm*—Burd, Braddock & Bartz

[57] ABSTRACT

A calf pulling device comprising an elongate rectangular shaft with a multiplicity of apertures formed therein along the length thereof, with a rotatable detachable breech spanner mounted on one end thereof, said shaft having a slidable jack mechanism mounted thereon, said jack mechanism including locking tongues and an operating handle and a chain hook whereby the jack mechanism can be progressively moved along said shaft by manipulation of said handle to steadily draw the calf from the cow and which can be quickly and instantaneously released from a rigid connection with the shaft to release the pressure on the calf whenever necessary to avoid injury thereto.

73 Claims, 10 Drawing Figures

CALF PULLER

When delivering animals of their young and particularly cows of their calves, the cow frequently needs assistance in the delivery through the medium of external pulling forces applied to the calf, particularly if the calf is not positioned properly. In addition, the calf must frequently be turned to provide the best delivery possible, all of which is difficult to do manually. As a result, some mechanical devices have been developed over the years to assist in pulling the calf from the mother, but each of the prior art devices developed to date have one or more deficiencies, and it is the general object of this invention to remedy many of these deficiencies by providing an improved calf pulling device. In many of the prior art devices, one of the primary difficulties in their design is that they either have no means for quickly releasing the tension on the calf or, if provided with some form of quick release mechanism, such mechanism is either too slow or too inconvenient to operate and normally requirers the use of two hands, which sometimes is quite difficult if only one person is assisting the delivery. Oftentimes, the calf may be strangled or otherwise injured during the delivery unless the tension is instantaneously released. Therefore, one of the most important objects of this invention is to prrovide a calf puller with a foolproof quick release mechanism which provides instantaneous and total release of tension and which can be operated by the use of only one hand in a convenient manner.

Another problem encountered with devices presently available is that the jack mechanism is capable of slipping, or at least tends to slip, during use and operation, which not only means that the operator is inconvenienced during use and requires more time than would otherwise be necessary, but also results in an erratic delivery which can be harmful or at least unduly painful to both the cow and the calf. Another important object of this invention, therefore, is to provide a calf puller with a novel jack mechanism which will not slip during use.

Still another problem associated with these devices is that the majority of them require the use of cables, which are bulky to handle and transport and inconvenient to use, and also present problems during use since they have a tendency to kink. Another object of this invention is to provide a calf pulling device which does not require the use of any cables whatsoever.

The cow can be most effectively assisted by working as close to the cow as possible. To date, most devices require that the work be done a substantial distance from the cow, and it is an object of this invention to provide a device which is not only simple in operation, but is compactly designed so that the work can be done close to the cow.

Still another problem with many available devices is that they are expensive to make and difficult to manipulate and transport and are oftentimes difficult to repair, requiring servicing at a special shop or factory outlet.

Another object of this invention is to provide a calf pulling device that is comprised of separate parts of lightweight construction which can be readily disassembled and compactly arranged for transport and storage and which can be quickly and easily assembled into its original form and which generally speaking can be repaired by the user without being taken to a specialty shop, and wherein only that part which needs servicing or repair can be taken in, with the remainder being left behind for convenience of transporting and handling.

Still another object of this invention is to provide a device which will permit a calf to be maneuvered during delivery and which provides a positive and steady rearward pull on the jack itself and the rotating spanner to provide the type of pulling tension and pulling angle considered most desirable during delivery.

Still another object is to provide a device whereby obstetrical chains can be used directly from the jack mechanism to the calf with no intermediary means required so that the chain can be hooked or connected directly to the pulling device.

These and other objects will be more fully understood and appreciated by an evaluation and reading of the following description made in conjunction with the attached drawings in which.

Figures 1, 2, 7, 8, 9, 10:
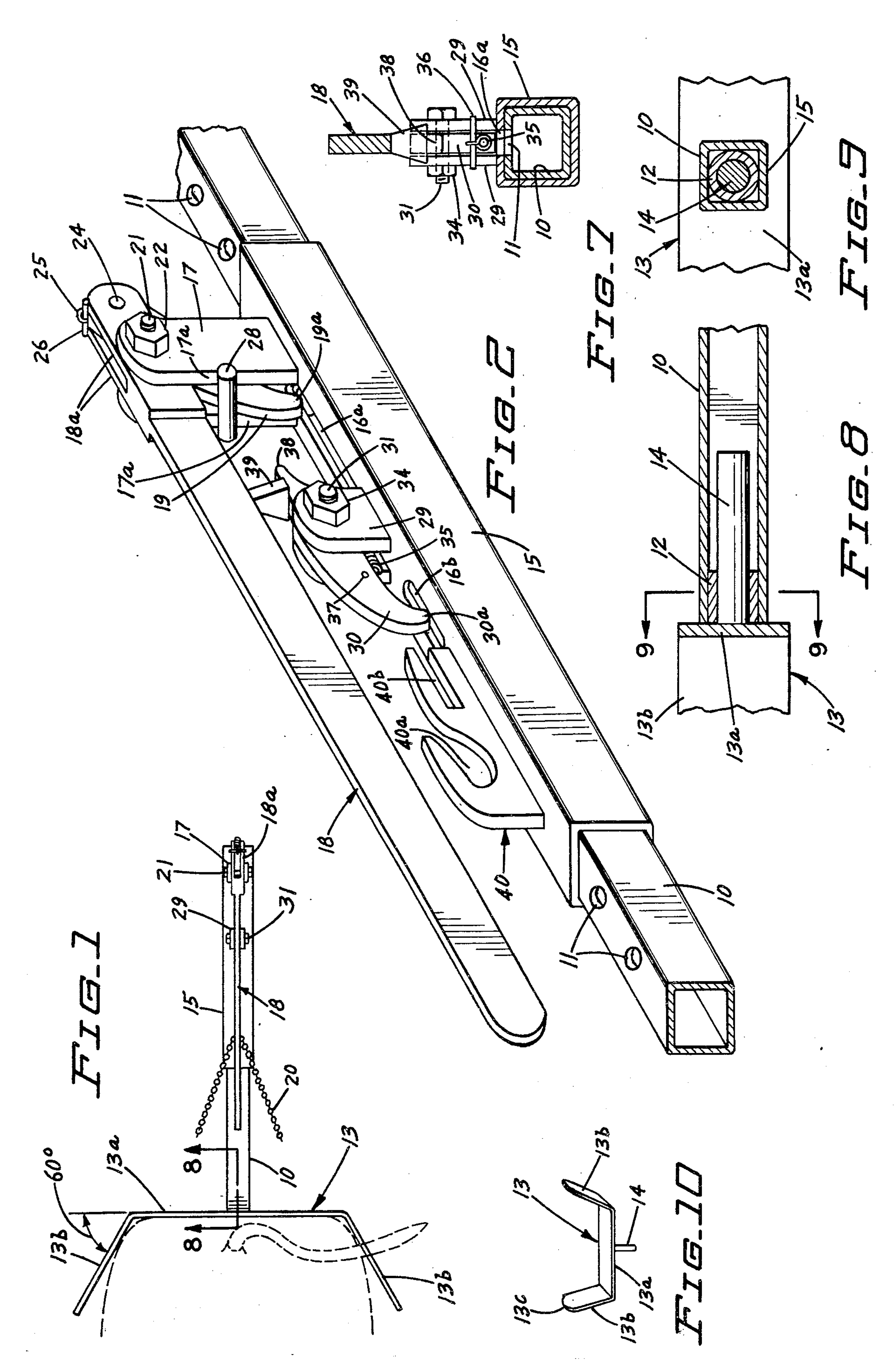
FIG. 1 is a top plan view of one preferred embodiment of this invention, illustrating actual use thereof during delivery while in engagement with the hindquarters of a cow.
FIG. 2 is a perspective view on an enlarged scale of the completely assembled jack mechanism portion of the calf pulling device illustrated in FIG. 1.
FIG. 7 is a cross sectional view taken along the line 7—7 of FIG. 3.
FIG. 8 is a longitudinal sectional view of the rotational connection between the breech spanner and the shaft as taken approximatetly along the line 8—8 of FIG. 1.
FIG. 9 is a cross sectional view taken along the line 9—9 of FIG. 8.
FIG. 10 is a perspective view of the breech spanner.
Figure 6:
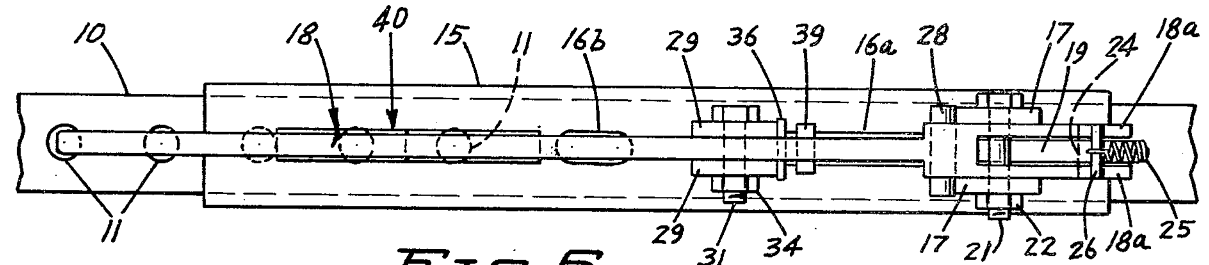
FIG. 6 is a top plan view of the device on an enlarged scale minus the breech spanner.

Although the use and application of the device of this invention is described and illustrated herein as applied to assisting in the delivery of a calf at birth, it will be understood that the use of the invention is not limited thereto, and its use as a mechanical jack can be utilized in any field of endeavor where such a device is needed, with or without modification, as the exigencies dictate.

REferring to the drawings, the calf puller illustrated therein includes a rectangular shaft or tube 10 which is preferably formed of square metallic tubing (preferably steel) with holes or openings 11 bored in one wall thereof and evenly spaced along the center line of one side, preferably the top thereof. The forward or proximal end (the end closest to the cow) of the shaft 10 is provided with a piece of round tubing 12 (preferably metallic) which is secured by any suitable means such as welding to the interior wall of the forward end of the shaft 10, said tubing 12 being adapted to receive the breech spanner 13 in a manner hereinafter described.

During use, the shaft 10 is stationary longitudinally, to provide the resistance against which the pulling portion of the device must work, although said shaft 10 is free to rotate 360° about its longitudinal axis.

The breech spanner 13 is preferably formed of a length of flat spring steel, said spanner consisting of a medial portion 13*a* and a pair of distal ends 13*b* disposed at an approximately 60° angle with respect to the medial portion 13*a*, with each of the distal end portions having a slightly rounded outer end 13*c*.

The medial portion 13*a* has affixed thereto by any suitable means a short length of round metallic stock forming a round shaft 14 (preferably steel) which extends in the opposite direction from the distal end portions of the spanner, the round shaft 14 being adapted to be removably inserted into the round tubular portion 12 of the shaft 10 whereby the spanner and the shaft are adapted to rotate freely relative to one another through 360° in a plane perpendicular to the shaft 10.

The spanner 13 is designed to span the rear of the cow with the ends 13*b* engaging and at least partially wrapping around the hindquarters of the cow, to hold the shaft 10 stationary longitudinally during delivery. In other applications, the spanner can be replaced by another type of shaft support which will be suitable for anchoring the shaft to the particular supporting base structure.

Thus, when not in use, the spanner 13 can easily be detached from the shaft 10 for compact packaging and storage.

The jack mechanism is mounted on the shaft 10 and includes an elongate slide or sleeve 15 formed of rectangular metal tubing, said slide functioning as a sleeve which rides on the shaft 10 and telescopically receives the same interiorly thereof. The interior dimensions of the slide 15 correspond approximately to the exterior dimensions of the shafat 10 whereby the shaft 10 and slide 15 are freely movable longitudinally with respect to each other and yet have minimum play or lateral movement therebetween. The top wall of the slide 15 has elongate slots 16*a* and 16*b* formed therein which extend longitudinally thereof and in alignment with the holes 11 of the shaft 10, a slot being provided for each of the locking tongues hereinafter described. Said slots 16*a* and 16*b* communicate with the interior of the slide 15 so that the locking tongues may enter the holes 11 disposed below said slots and engage the shaft 10 either to provide the leverage necessary to move the slide relative to the shaft away from the cow, or hold it against movement towards the cow.

Adjacent one (distal) end of the slide, a pair of upstanding handle or lever supporting and guide members 17 are provided which are rigidly secured to the sleeve in any suitable fashion. The members 17 are laterally spaced apart to receive the lever handle 18 therebetween as well as levering tongue 19 which constitute a part of the lever member, said members 17 not only supporting the handle but also serving to guide the vertical movements of said handle and said levering tongue 19, which also is a levering element.

The lever supporting members 17 are provided with aligned openings in which openings is installed a threaded pivot pin 21, with a fastener such as a nut 22 being used to removably secure said pivot pin to said members 17.

The handle 18 has a bifurcated end portion consisting of the opposing spaced apart arms 18*a* having aligned openings formed therein which also receive the pivot pin 21 for free rotational movement of the handle 18 and said arms 18*a* relative to said pivot pin about the longitudinal axis of said pivot pin, which serves as the fulcrum for the lever.

The tongue 19 is pivotally attached to the bifurcated end of the handle by means of a pivot pin 24 installed in aligned openings with the bifurcated portions 18*a* of the handle which extends transversely of the arms 18*a* with the tongue 19 being swingably disposed in the space between the arms 18*a* for swinging movement about pin 24. A helically coiled contracting spring 25 is provided, the upper end of which is secured to a cross bar 26 attached to and extending between the arms 18*a*, the other end of said spring 25 being attached to said tongue by installing the loop of the lower end thereof in an opening 27 in tongue 19 whereby the tongue 19 is continually biased or pulled downwardly and forwardly towards said slide 15 and shaft 10 under the influence of said spring.

The tongue 19 is provided with a pointed or tapered lower end or tip 19*a* which points or faces downwardly and is disposed in alignment with the slot 16*a* and intended to selectively engage the holes 11 in the shaft 10. The upper edge of the tongue 19 is provided with an elongate elevating bar 28 which extends laterally or transversely of said tongue and is adapted to engage the leading edge or track surface 17*a* of the members 17 so that the rearward (counterclockwise as seen in the drawings) throw of the handle 18 towards the cow elevates the levering tongue 19 thereby causing it to disengage from the shaft 10.

It will be understood that the tongue 19 is an essential part of the lever or leverage system comprising the handle 18 and the tongue 19, for it is the action of tongue 19 against the stationary shaft 10 under the influence of the handle 18 swinging forwardly away from the cow (clockwise in the drawings) which causes the sleeve 15 to slide forwardly away from the cow and exert a pulling force on the obstetrical chain 20, the ends of which are attached to the calf (normally to the front feet) to assist in pulling it from the cow.

A second group of locking mechanisms similar to, but slightly smaller than that previously described is provided adjacent the middle portion of the slide and includes a pair of upstanding spaced apart opposed tongue supporting members 29 which are similar to members 17 but substantially smaller and shsorter in height, said members 29 being rigidly attached to sleeve 15 to pivotally or swingably support a locking tongue 30 therebetween, the pivotal mounting of said tongue on said members being provided by a pivot pin 31 which may be a bolt or some other form of pivot pin extending through aligned openings in the tongue supporting members 29 and in the locking tongue itself, the pivot pin 31 being removably secured to the members 29 by means of any suitable fastener such as the threaded nut 34.

A second helically coiled contracting spring 35 is provided, one end of which is attached to a cross bar 36 affixed to and extending transversely of the members 29, and the other end of said spring being attached to the tongue by installation in an opening 37 provided therein whhereby the tapered and pointed end or tip 30*a* of the tongue is continuously biased or pulled downwardly and forwardly away from the cow towards the slide 15 and shaft 10 by means of said spring 35.

The tongue 30 is strictly a locking member, and plays no part in exerting any leverage or pulling force on the slide 15. The lower tip 30*a* thereof is intended to insert itself in one of the openings 11 in the shaft 10 as the tongue 19 is inserted in another of the openings 11 ahead of the opening in which tongue 30 is inserted. When the tongue 19 is lifted from engagement with shaft 10, tongue 30 remains in its opening and in engagement with shaft 10, preventing the sleeve from slipping or sliding backwards and thereby losing some of the distance already gained. Although the tongue 30 prevents retractive movement towards the cow, it is adapted to freely release itself from the shaft 10 anytime there is a forward movement of the slide 15 relative to shaft 10 (as used herein, the term "forward" refers to a direction away from the cow and base support and "rearward" means movement towards the cow or base support).

Figure 3:
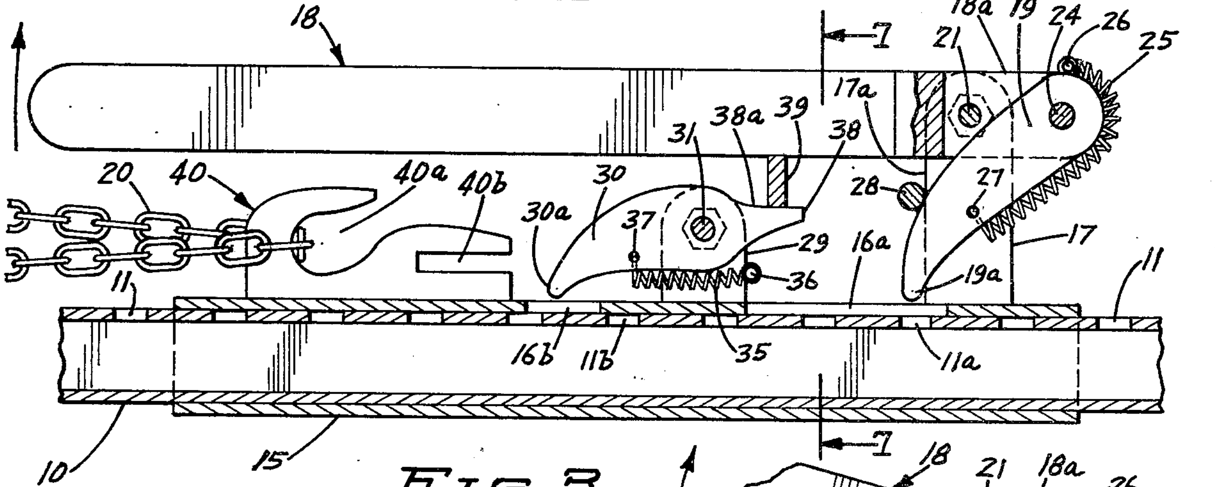
FIG. 3 is a side elevational view of the device with the locking tongues released for free travel of the jack mechanism on the supporting shaft.

The end of locking tongue 30 opposite that of the pointed end is provided with a dog 38, the top surface 38*a* thereof being adapted to be engaged by a releasing member 39 which is affixed to and extends from the handle 18 to release the tongue 30 from engagement with the shaft 10 when the handle 18 is lowered to a position approximately paralleling the slide 15 and shaft 10 as illustrated in FIGS. 2 and 3, which is the fully retracted or starting position of the handle 18.

Thus, if for any reason the tongue 30 must be unlocked, or the slide 15 returned to free sliding capabilities in both directions, or if the tension on the calf or obstetrical chain needs instant relief or release, this can be immediately accomplished by quickly swinging handle 18 back to the starting position of FIGS. 2 and 3, thereby releasing both tongues 19 and 30 and unlocking the slide 15 for free longitudinal movement on shaft 10 in either direction.

Release member 39 works against the biasing action of spring 35, and swings the tongue upwardly (clockwise as illustrated) away from engagement with shaft 10. Thus, the operator can single-handedly release the entire mechanism or progressively jack or pull the calf while his other hand is used to position and steady the distal end.

The other end portion of the slide 15 is provided with an obstetrical chain hook 40 which is designed so as to provide both a loop hook 40*a* and a grab hook 40*b* for added versatility for the use of obstetrical chains with this device.

Figure 4:
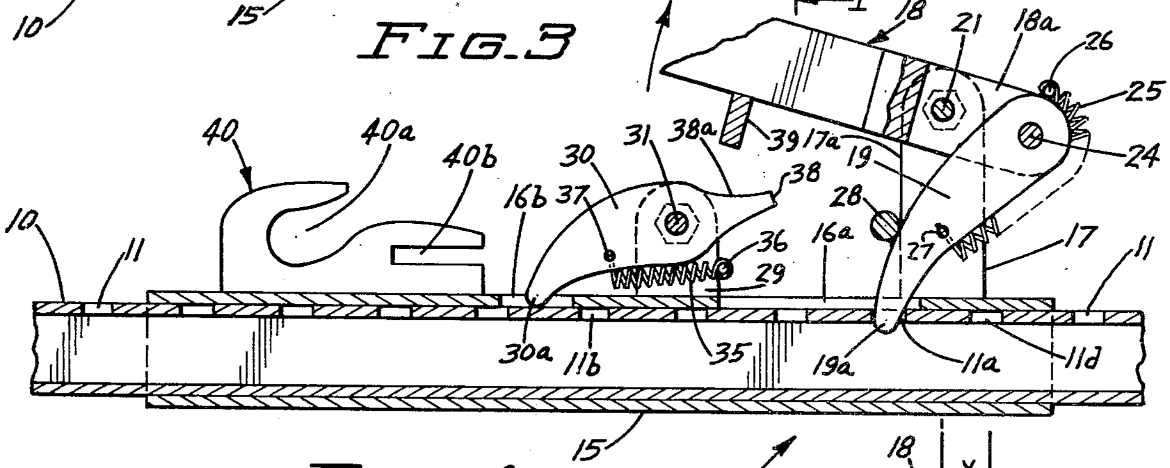
FIG. 4 is a side elevational view of the device of this invention with the handle in a partially raised pulling position with the primary locking and levering tongue engaged with the supporting shaft to pull the slide on the shaft and prevent movement of the jack mechanism relative thereto, with the secondary locking tongue not yet engaged.
Figure 5:
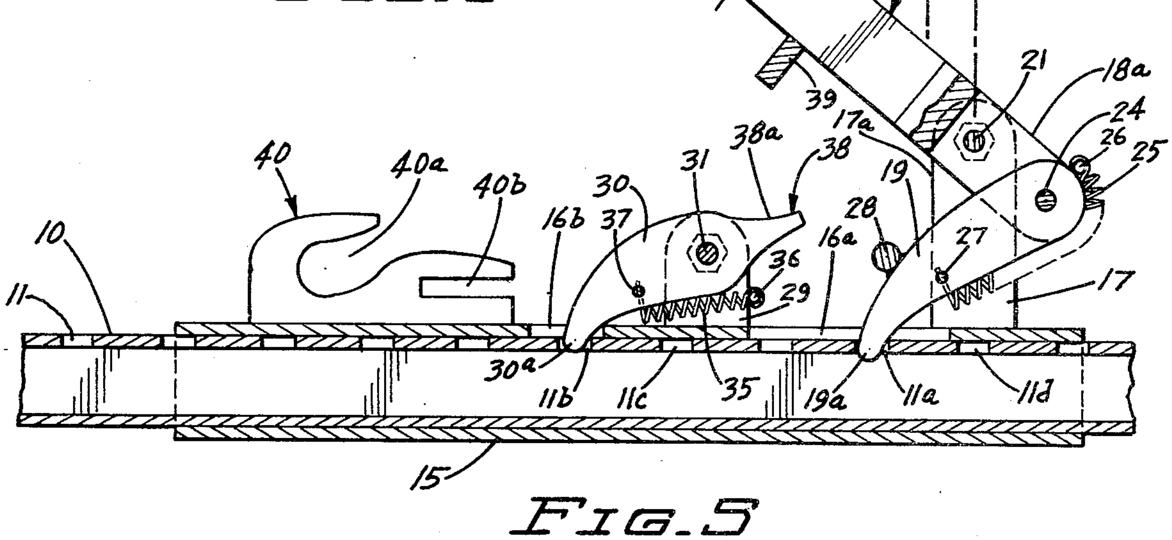
FIG. 5 is a side elevational view with the handle raised further than in FIG. 4, with the secondary locking tongue in locking engagement with the stationary shaft to prevent slippage.

FIGS. 3, 4 and 5 illustrate the progressive steps and incremental movements of the device during one forward swing of the handle 18. FIG. 3 shows the component parts in their initial completely unlocked position, with the tongues 19 and 30 completely disengaged and the handle 18 in fully retracted starting position, and the sleeve 15 free to move longitudinally in either direction on the shaft 10. Note that the tips 19*a* and 30*a* of the tongues are above the top level of sleeve 15 and aligned with their respective slots 16*a* and 16*b*.

FIG. 4 shows the device and its components after the handle 18 has been partially raised and swung forwardly (clockwise). This movement has pushed the tip 19*a* of tongue 19 downward through slot 16*a* in sleeve 15 into opening 11*a* in shaft 10 with elevating bar 28 controlling the downward movement through its engagement with edges 17*a*, the bar 28 being held against the edges 17*a* by the biasing action of spring 25.

This same movement has lifted release member 39 from engagement with dog 38, permitting tongue 30 to come under the influence of spring 35, which has pulled it downwardly through its sleeve slot 16*b* into engagement with the portion of the top wall or side of shaft 10 immediately preceding shaft opening 11*b*.

The openings 11 are smaller than the major portion of tongue 19, but larger than tips 19*a* (and 30*a*) so as to permit end 19*a* to penetrate sufficiently to make adequate levering engagement with shaft 10. When tip 19*a* can penetrate no further, then the levering or pulling action begins.

FIG. 5 illustrates the device during the levering or pulling action, the handle 18 having been lifted forwardly still further from its position in FIG. 4. As the handle continued its movement from its FIG. 4 position, the levering tongue 19 was anchored against shaft 10, so that continued movement of handle 18 forced members 17 forwardly to the position of FIG. 5, pulling sleeve 15 the same distance, as illustrated by the incremental distance X. This movement has also brought tip 30*a* of tongue 30 into alignment with opening 11*b* in the shaft, and spring 35 has pulled tip 30*a* downward into opening 11*b* and into engagement with shaft 10, so that the sleeve 15 cannot slip rearwardly if handle 18 is released by the operator, or if handle 18 is swung rearwardly to initiate another pulling movement, tongue 30 holding the sleeve against any such movement.

To repeat the operation, the handle is swung rearwardly (counterclockwise) preferably to a point just short of engagement of release member 39 with dog 38, and then swung forwardly again to move the slide and the calf the distance X. As this movement is repeated, tongue 30 automatically disengages itself from opening 11*b* under the influence of the sleeve moving forward, and moves towards the next opening 11*c* in the series, as tongue 19 moves towards its next adjacent opening 11*d* in the series.

In use and operation, the breech spanner is positioned against the hindquarters of the cow, and the ends of the chain 20 are attached to the front legs of the calf, with the medial portions of the chain engaging the hook 40.

The operator then begins operating handle 18, moving it back and forth as illustrated and hereinbefore described moving the calf the distance X each time. If problems arise, or if for any reason the tension on the calf must be alleviated, the operator can immediately move the handle to starting position, lifting both tongues out of engagement with the shaft 10 and permitting sleeve 15 to slide rearwardly to whatever degree is necessary to eliminate the problem.

It will be noted that pivot pins 21 and 31 are self-explanatory and it will also be noted that the pivot pin 24 is located on one side (forwardly) of the pivot axis provided by pivot pin 21, and that the elevating bar 28 is located on the opposite (rearward) side of the pivot axis of pin 21, and it will further be noted that said pivot pin 24 and elevating bar 28 are also located on opposite sides of the lever supporting members 17. These relative locations of these parts enables the elevating bar 28 to engage the track surfaces 17*a* and raise the levering tongue 19 from engagement with the main supporting shaft 10 when the handle is swung rearwardly (counterclockwise) towards starting position. Thus, it will be appreciated that this invention includes a unique and effective leverage system comprising the handle 18 and the tongue 19 and the various supporting structure therefore, the design of said leverage system providing maximum leverage and ease of operation of the jack mechanism within a relatively small range of movement of the handle so that the operator can maintain a position close to the calf being born during substanatially the entire delivery operation.

It will also be understood that parts of the description which indicate a directional orientation such as up, upstanding, down, etc., and specific directions of movemennts such as forward, rearward, counterclockwise, etc., have relevancy only insofar as the device is presented in the accompanying drawings and it is not intended that the invention or the claims be limited insofar as these specific directional descriptions or limitations are concerned, but only insofar as they relate to the remainder of the structure and the functioning thereof.

Thus, considering the invention in its broader aspects, it involves a force exerting mechanism which includes a supporting means such as the tube 10, movable means such as sleeve 15 supported by said supporting means, means including the leverage system involving the handle 18 and tongue 19 for moving said movable means relative to said supporting means, attachment means such as the hook structure 40 carried by the movable means, the attachment means being adapted for connection to the object on which the force is to be exerted (such as the calf to be delivered) by any suitable pulling means such as the obstetrical chain 20 and having locking means including the tongue 30 for holding the supporting and movable means against movement relative to one another with release means such as the release member 39 for releasing the locking means in response to the actuation of the handle portion of the moving means with the supporting means having a series of detents such as the openings 11 formed therein and also including base means such as the breech spanner 13 for supporting and holding the supporting means against movement in at least one direction, which in this case is towards the cow itself.

Thus, the entire jack mechanism can be continuously and progressively cranked outwardly away from the cow without any danger of slippage and yet can be quickly and instantaneously released from connection with the supporting shaft 10 so as to immediately and instantaneously relieve the tension on the obstetrical chain 20 and on the calf itself to prevent any injury thereto.

It will, of course, be understood that various modifications, variations and changes may be made in the form, details, proportions, dimensions and arrangements shown and set forth herein without departing from the spirit and scope of the invention hereof, which scope is defined by the claims attached hereto and included herein, and the appended claims should be construed as broadly as possible in view of the prior art, the specific embodiments described herein being given by way of example only for clearness of understanding, and no unnecessary limitations should be derived therefrom.

The embodiments of the invention in which an exclusive property or privilege is claimed are defined as follows:

1. Force exerting mechanism comprising:

supporting means, movable means supported by said supporting means, said movable means including lever means for moving said movable means relative to said supporting means, said lever means including a handle swingable between a first position in which the lever means are deactivated and a second position in which the lever means cause said movable means to move relative to said supporting means, attachment means carried by said movable means, said attachment means being adapted for connection to an object on which said force is to be exerted, movement of said movable means relative to said supporting means in one direction transmitting a force in the same direction through said attachment means to said object, locking means for releasably holding said supporting means and movable means against movement relative to one another in at least one direction, said locking means including a locking member swingable into and out of engagement with said supporting means, said locking member when engaged with the supporting means holding said supporting means and movable means against movement relative to each other in one direction while permitting relative movement between the supporting means and movable means in the opposite direction, a pair of opposed spaced apart supporting elements mounted on said movable means for said locking member, means pivotally supporting said locking member between said supporting elements for swinging movement therebetween, spring means biasing said locking member towards locking engagement with said supporting means, said spring means having two end portions, one end portion being attached to said locking member, the other end portion being attached to said supporting element, release means carried by said handle for releasing said locking means in response to the actuation of said lever means, said release means being adapted to engage said locking member when said locking member is in engagement with said supporting means and swing it out of engagement with said supporting means, and said engagement of said release means and locking member taking place as said handle moves toward said first position.

2. The mechanism of claim 1, wherein said spring means is an elongate helically coiled spring, and wherein said one end portion is anchored to an opening in said locking member and said other end portion is connected with a cross bar extending between said supporting elements.

3. A force exerting mechanism comprising:

supporting means having a series of detents formed therein, movable means supported by said supporting means and telescopically engaged therewith, said movable means including lever means for moving said movable means relative to said supporting means, said lever means including a handle swingable between a first position in which the lever means are deactivated and a second position in which the lever means cause said movable means to move relative to said supporting means, said movable means also including a tubular sleeve slidably mounted on said supporting means, said sleeve having an opening therein aligned with said detents, attachment means carried by said movable means, said attachment means being adapted for connection with an object on which said force is to be exerted whereby movement of said movable means relative to said supporting means in one direrction transmits a forcce in the same direction through said attachment means to said object, locking means for releasably holding said supporting means and movable means against movement relative to one another in at least one direction, said locking means including a locking member swingable into and out of engagement with the detents on said supporting means, said locking member when engaged with said detents holding said supporting means and movable means against movement relative to each other in one direction while permitting relative movement between said supporting means and movable means in the opposite direction, said locking member being adapted to move through said opening into and out of engagement with said detents, said locking member when in engagement with said detents preventing movement of said sleeve relative to said supporting means in said one direction, means mounted on said movable means for supporting said locking member, means pivotally supporting said locking member on said means on said movable means for swinging movement toward and away from said detents, spring means biasing said locking member towards locking engagement with said detents, release means for releasing said locking means in response to the actuation of said lever means, said relase means being carried by said handle and adapted to engage said locking member when said locking member is in engagement with said detents and swing it out of engagement with said supporting means, and said engagement of said release means and locking member taking place as said handle moves toward the first position.

4. The mechanism of claim 3, wherein:

said locking member is an elongate member having first and second end portions, said first end portion being adapted to engage said detents to prevent movement between said movable means and said supporting means, said release means being adapted to engage said second end portion and cause pivotal movement of said locking member in a direction away from locking engagement with said detents.

5. The mechanism of claim 3, wherein said supporting means is a tubular member, and said detents are openings formed in said tubular member.

6. The mechanism of claim 5, wherein said tubular member and tubular sleeve are square in cross section.

7. The mechanism of claim 6, wherein said lever means is adapted to move back and forth through the apertures of said movable means and to move into and out of levering engagement with the apertures of said supporting means.

8. The mechanism of claim 3, including structure attachable to said supporting means for holding said supporting means against the hindquarters of a female animal when giving birth to her young, and flexible means adapted to be attached to said attachment means and the legs of the baby during delivery.

9. The mechanism of claim 8 including:

means mounting the structure on the supporting means whereby said supporting means is rotatable through 360° of movement relative to said structure.

10. A force exerting mechanism comprising:

supporting means, movable means supported by said supporting means, means for moving said movable means relative to said supporting means, said means for moving said movable means including levering means, said levering means including an elongate handle member pivotally mounted on said movable means, said levering means also including a levering element pivotally attached to said handle member, said levering element being adapted to be moved into and out of levering engagement with said supporting means by the swinging movement of said handle, attachment means carried by said movable means, said attachment means being adapted to be connected with an object on which said force is to be exerted, movement of said movable means relative to said supporting means in one direction transmitting a force in the same direction through said attachment means to said object, locking means for releasably holding said supporting means and movable means against movement relative to one another in at least one direction, release means mounted on said handle for releasing said locking means in response to the actuation of said moving means, said handle being swingable between first and second positions, said levering element being out of engagement with said supporting means when said handle is in said first position, said release means being in engagement with said locking means and holding the same out of engagement with said supporting means when said handle is in said first position,

11. The mechanism of claim 10, including first guide means mounted on said levering element and second guide means connected with said movable means, said guide means being adapted to engage each other during the course of movement of said handle from said second to said first position, the engagement of said guide means contributing to the movement of said levering element away from engagement with said supporting means.

12. The mechanism of claim 11, including spring means biasing said levering element towards engagement with said supporting means, said guide means when engaging each other working against the biasing action of said spring means.

13. A force exerting mechanism comprising:

tubular supporting means provided with apertures which function as detent means, movable means supported by said supporting means, means for moving said movable means relative to said supporting means, said moving means engageable with said detent means, attachment means carried by said movable means, said attachment means being adapted for connection to an object on which said force is to be exerted, movement of said movable means relative to said supporting means in one direction transmitting a force in the same direction through said attachment means to said object, locking means for releasably holding said supporting means and movable means against movement relative to one another in at least one direction, and release means for releasing said locking means in response to the actuation of said moving means.

said handle, as it moves from said first to said second position, moving said release means out of engagement with said locking means and moving said levering element into levering engagement with said supporting means, continued movement of said handle towards said second position after said levering element is in levering engagement with said supporting means causing said movable means to move relative to said supporting means.

14. The mechhanism of claim 13 wherein both said supporting means and said movable means are provided with aperture means for receiving said means for moving said movable means, said aperture means of said movable means being aligned for at least periodic registration with the apertures of said supporting means, said means for moving said movable means being adapted to move through the aperture means of said movable means to engage the structure of said supporting means defining the aperture of said supporting means whereby said movable means is moved relative to said supporting means by the resistance encountered by said moving means when installed in the aperture of said suppporting means and working thereagainst.

15. The mechanism of claim 13 wherein said movable means is an elongate tubular member of rectangular cross section, and wherein said supporting means is an elongate member of rectangular cross section.

and wherein said elongate members are in telescopic engagement with each other with said supporting means being located interiorly of said movable means, both said supporting means and said movable means having apertures formed therein which are adapted for at least periodic registration with one another, said means for moving said movable means being adapted for movement through the aperture means of said movable means for installation in the aperture means of said supporting means and adapted to engage at least a portion of the supporting means defining its aperture means whereby the resistance encountered effects movement of said movable means relative to said supporting means.

16. The mechanism of claim 13 wherein said means for moving said movable means includes lever means, said lever means being pivotally supported by said movable means, said lever means being adapted to engage said supporting means and move said movable means in response to pivotal movement of said lever means in one direction.

17. The mechanism of claim 16, wherein said lever means includes first and second parts, said first part being swingable about a first pivot axis which is in a fixed relationship with said movable means, said second part being pivotally attached to said first part for movement about a second pivot axis, said second part being adapted to move into and out of levering engagement with said supporting means.

18. The mechanism of claim 17 including spring means continuously biasing said second part towards levering engagement with said supporting means.

19. The mechanism of claim 17, including track means supported by said movable means, and guide means carried by said second part adapted to engage said track means for guiding the movements of said second part.

20. The mechanism of claim 19 wherein said track means are rigidly connected to said movable means, and wherein said first part is pivotally mounted on said track means.

21. The mechanism of claim 17, including lever supporting means carried by said movable means, said lever supporting means pivotally supporting said first part for rotation about said first pivot axis, said lever supporting means providing a track, and guide means carried by said second part adapted to engage said track to guide the movements of said second part relative to said supporting means.

22. The mechanism of claim 21, including means biasing said guide means toward engagement with said track.

23. The mechanism of claim 21, wherein said second pivot axis is disposed on one side of said first pivot axis and said track and guide means are disposed on the opposite side of said first pivot axis.

24. The mechanism of claim 21, wherein said lever supporting means comprises a pair of opposed spaced apart lever supporting elements with said first part pivotally mounted therebetween for swinging movement relative thereto, said elements supporting said first part for pivotal movement about said first axis, one side of each of said elements providing a track located on one side of said first pivot axis, said second axis being located on the opposite side of said first pivot axis from said track, a guide element carried by said second part and transverse to said track and adapted to engage both of said tracks to guide the movement of said second part relative to said supporting means, and spring means biasing said guide element towards engagement with said track.

25. The mechanism of claim 13 wherein: the means for moving the movable means includes lever means movable between a disengagement position in which the supporting means and movable means are fully disengaged and a levering position in which the lever means is adapted to move said movable means relative to said supporting means by leverage, said lever means including release means adapted to engage and hold said locking means out of engagement with said supporting means when said lever means is in full disengagement position, said release means being further adapted to release said locking means for engagement with said support means when said lever means is swung from its fully disengaged position towards its levering position.

26. The mechanism of claim 1 wherein said attachment means includes at least one slot for receiving and holding a chain.

27. The mechanism of claim 1 wherein said attachment means includes a grab hook and a loop hook for engaging and holding a chain.

28. The mechanism of claim 1, including base means for said supporting means, and wherein said base means is a yoke-shaped element adapted to receive said supporting surface between the arms thereof.

29. The mechanism of claim 1, including base means for said supporting means, and wherein said base means and said supporting means are capable of rotation relative to one another.

30. The mechanism of claim 1, including base means for said supporting means, and wherein said supporting means has a cylindrical portion at one end thereof, and wherein said base means includes a cylindrical element adapted for telescopic engagement with said cylindrical portion of said supporting means whereby said base means and supporting means are adapted for rotational movement relative to one another about the longitudinal axes of said cylindrical elements.

31. The mechanism of claim 1, wherein said supporting means and movable means are both elongate and telescopically engaged for longitudinal movement relative to one another.

32. The mechanism of claim 16, including locking means for releasably holding said supporting means and movable means against movement relative to one another in at least one direction.

33. The mechanism of claim 32, including attachment means adapted to engage and hold a flexible pulling element and transmit the force to be exerted to said pulling element.

34. The mechanism of claim 3, including attachment means adapted to engage and hold a flexible pulling element and transmit the force to be exerted to said pulling element.

35. The mechanism of claim 3, including base means for said supporting means, said base means being adapted to engage a supporting surface and prevent movement of said supporting means in a direction opposite to said one direction when said mechanism is in operation, said base means and said supporting means being adapted for relative rotation therebetween.

36. The mechanism of claim 16, wherein said supporting means and movable means are both elongate and telescopically engaged for longitudinal movement relative to one another, detent means carried by said supporting means, said lever means being adapted to engage said detent means and move said movable means relative to said supporting means when moved in said one direction, said lever means being adapted to disengage said detent means and said supporting means when moved in the opposite direction.

37. The mechanism of claim 36, including attachment means adapted to engage and hold a flexible pulling element and transmit the force to be exerted to said pulling element.

38. The mechanism of claim 37, including base means for said supporting means, said base means being adapted to engage a supporting surface and prevent movement of said supporting means in a direction opposite to said one direction when said mechanism is in operation, said base means and said supporting means being adapted for relative rotation therebetween.

39. The mechanism of claim 16, including attachment means adapted to engage and hold a flexible pulling element and transmit the force to be exerted to said pulling element.

40. The mechanism of claim 39, including base means for said supporting means, said base means being adapted to engage a supporting surface and prevent movement of said supporting means in a direction opposite to said one direction when said mechanism is in operation, said base means and said supporting means being adapted for relative rotation therebetween.

41. The mechanism of claim 16, including base means for said supporting means, said base means being adapted to engage a supporting surface and prevent movement of said supporting means in a direction opposite to said one direction when said mechanism is in operation, said base means and said supporting means being adapted for relative rotation therebetween.

42. The mechanism of claim 32, wherein said supporting means and movable means are both elongate and telescopically engaged for longitudinal movement relative to one another.

43. The mechanism of claim 42, including attachment means adapted to engage and hold a flexible pulling element and transmit the force to be exerted to said pulling element.

44. The mechanism of claim 43, including base means for said supporting means, said base means being adapted to engage a supporting surface and prevent movement of said supporting means in a direction opposite to said one direction when said mechanism is in operation, said base means and said supporting means being adapted for relative rotation therebetween.

45. The mechanism of claim 32, including base means for said supporting means, said base means being adapted to engage a supporting surface and prevent movement of said supporting means in a direction opposite to said one direction when said mechanism is in operation, said base means and said supporting means being adapted for relative rotation therebetween.

46. The mechanism of claim 36, including base means for said supporting means, said base means being adapted to engage a supporting surface and prevent movement of said supporting means in a direction opposite to said one direction when said mechanism is in operation, said base means and said supporting means being adapted for relative rotation therebetween.

47. The mechanism of claim 1, wherein said supporting means is in telescopic relationship with said movable means, and including base means for said supporting means, said base means being adapted to engage a supporting surface and prevent movement of said supporting means in a direction opposite to said one direction when said mechanism is in operation, said base means and said supporting means being adapted for relative rotation therebetween.

48. The mechanism of claim 31, including attachment means adapted to engage and hold a flexible pulling element and transmit the force to be exerted to said pulling element.

49. The mechanism of claim 31, including base means for said supporting means, said base means being adapted to engage a supporting surface and prevent movement of said supporting means in a direction opposite to said one direction when said mechanism is in operation, said base means and said supporting means being adapted for relative rotation therebetween.

50. The mechanism of claim 34, including base means for said supporting means, said base means being adapted to engage a supporting surface and prevent movement of said supporting means in a direction opposite to said one direction when said mechanism is in operation, said base means and said supporting means being adapted for relative rotation therebetween.

51. The mechanism of claim 42, including base means for said supporting means, said base means being adapted to engage a supporting surface and prevent movement of said supporting means in a direction opposite to said one direction when said mechanism is in operation, said base means and said supporting means being adapted for relative rotation therebetween.

52. A force exerting mechanism comprising:

supporting means, movable means supported by said supporting means, means for moving said movable means relative to said supporting means, attachment means carried by said movable means, said attachment means being adapted for connection to an object in which said force is to be exerted, movement of said movable means relative to said supporting means in one direction transmitting force in the same direction thhrough said attachment means to said object, said supporting means comprising an elongate tubular member of square cross section having a series of apertures formed therein and extending longitudinally thereof, said member having a proximal and a distal end portion, said proximal end having a cylindrical element mounted interiorly of said member, said mechanism including base means for holding and positioning said mechanism against the hindquarters of a cow, so that said member extends generally rearwardly from the hindquarters of said cow with the distal end portion of said member being the end furthest removed from said hindquarters, said base means including a yoke portion adapted to receive said hindquarters, said yoke portion having a cylindrical portion attached thereto and extending rearwardly therefrom and adapted to telescopically engage each said cylindrical element for relative rotation of said yoke portion and elongate tubular supporting member relative to one another, said movable means including an elongate sleeve of square cross section in removable telescopic engagement with said tubular supporting member and freely slidable relative thereto longitudinally thereof, said sleeve having proximal and distal end portions with respect to their relationship to the hindquarters of said cow, the proximal end portion having rigidly mounted thereon hook means for engaging and holding a chain, the distal end portion of said sleeve having a pair of spaced apart lever supporting elements, an elongate lever mounted on said lever supporting elements for pivotal movement relative thereto between a first completely disengaged position and a second engaged position representing the termination of said force to be exerted during any single pulling movement of said lever, upstanding spaced apart locking element supporting means mounted on said movable member and located between said attachment means and the supporting elements for said lever along the length of said sleeve, first slot means formed in said sleeve between said lever supporting elements and said lock supporting element and second slot means formed in said sleeve between said lock supporting elements and said attachment means, a levering element disposed between said lever supporting elements, said levering element being pivotally connected to one end portion of said lever and adapted for pivotal movement relative thereto about an axis different from the pivot axis of said lever, said lever element having an end portion adapted to move through said first slot means in said sleeve to engage the apertures of said supporting member so as to provide the resistance necessary to enable said sleeve to move relative to said supporting member when said lever is swung between the aforementioned operational positions, said levering element having a guide element disposed generally transversely thereof and adapted to engage said upstanding lever supporting members, spring means extending between said lever means and said levering element continuously biasing said levering element towards engagement with the apertures of said supporting member and continuously biasing said guide member towards engagement with said upstanding lever supporting element, said locking means including a locking element pivotally mounted on and supported by said upstanding locking element supporting elements and pivotally mounted relative thereto and therebetween, one end portion of said locking element being adapted to move back and forth through said second slot means in said sleeve, said locking element having one end portion adapted to move through said second slot means in said sleeve into and out of engagement with an aperture of said supporting means and adapted to engage one of said apertures when said lever means discontinues movement to prevent said sleeve from moving in the direction of the proximal end of said supporting member while permitting free movement of said sleeve in the direction of the distal end of said supporting member, spring means extending between said locking element supporting elements and said locking element continuously biasing said locking element towards engagement with said supporting member, said lever means including an operational handle, said handle having a control element mounted thereon, said control element being adapted to engage said locking element and lift it from and hold it against engagement with said supporting member when said lever is in said first non-levering position, and said control element being further adapted to release said locking element for movement towards said supporting member as said levering means moves from said first to said second positions.

53. An apparatus for assisting an animal to give birth to a fetus comprising: first means adapted to be positioned in engagement with the animal, second means movably mounted on the first means for movement in a direction away from the first means and the animal, third means operably connecting the first means and the second means, said third means being operable to move the second means in said direction when the first means is in engagement with the animal, and fourth means connecting the second means with the fetus whereby movement of the second means in said direction will hold the first means in engagement with the animal and assist the animal in giving birth to the fetus.

54. The apparatus of claim 53 wherein: said first means includes a supporting means having an elongated member, a spanner mounted on the elongated member, said spanner being adapted to be positioned in engagement with the animal, and means mounting the spanner on the elongated member.

55. The apparatus of claim 54 wherein: said spanner comprises a generally U-shaped member having a transverse base and adapted to engage the animal and end portions integral with the opposite ends of the base adapted to be located adjacent opposite sides of the animal, said means connecting the spanner to the elongated member being connected to the base.

56. The apparatus of claim 54 wherein: the means connecting the elongated member to the spanner comprises a shaft mounted on the spanner and a tubular member mounted on the elongated member, said shaft being rotatably positioned in said tubular member whereby said spanner can rotate relative to the elongated member and removed from the elongated member.

57. The apparatus of claim 53 wherein: the first means includes an elongated linear member, and said second means includes an elongated tubular member slidably mounted on the linear member.

58. The apparatus of claim 57 wherein: said third means comprises a first tongue movably mounted on the second means, and a second tongue movably mounted on the second means to limit the movement of the second means relative to the first means to one direction, handle means operatively connected to the first tongue to move said first tongue relative to the linear member, said linear member having a plurality of linearly aligned openings adapted to accommodate a portion of the first tongue whereby on movement of the first tongue the tubular member is moved relative to the linear member.

59. The apparatus of claim 58 including: means on said handle engageable with the second tongue to move said second tongue in an inoperative position.

60. The apparatus of claim 57 including: a hook secured to the tubular member, said fourth means comprising an elongated flexible means connected to the hook and attachable to the fetus.

61. An apparatus for assisting an animal to give birth to a fetus comprising: an elongated linear supporting member, a spanner located adjacent one end of the supporting member, means mounting a mid-portion of the spanner on the supporting member, said supporting member having longitudinal series of detents, a movable member supported by said supporting member and telescopically engaged therewith, said movable member having means adapted to accommodate structure attachable to the fetus, and ratchet means mounted on the movable member and engageable with said detents operable to move the movable member with respect to the supporting member whereby the spanner engages the animal and the structure will apply a pulling force on the fetus responsive to movement of the tubular member to assist the animal in giving birth to the fetus.

62. The apparatus of claim 61 wherein: said spanner comprises a generally U-shaped member having a transverse base and adapted to engage the animal and end portions integral with the opposite ends of the base adapted to be located adjacent opposite sides of the animal, said means mounting the spanner to the supporting member being connected to the base.

63. The apparatus of claim 61 wherein: the means mounting the spanner on the supporting member comprises a shaft mounted on the spanner and a tubular member mounted on the supporting member, said shaft being rotatably positioned in said tubular member whereby said spanner can rotate relative to and removed from the supporting member.

64. The apparatus of claim 61 wherein: said movable member is an elongated tubular member slidably mounted on the supporting member.

65. The apparatus of claim 61 wherein: said ratchet means comprises a first tongue movably mounted on the movable member, and a second tongue movably mounted on the movable member and engageable with the detents to limit movement of the movable member relative to the supporting member to one direction, handle means operatively connected to the first tongue to move said first tongue into engagement with the detents whereby on movement of the first tongue the tubular member is moved relative to the supporting member.

66. The apparatus of claim 65 including: means on said handle engageable with the second tongue to move said second tongue in an inoperative position.

67. The apparatus of claim 61 including: a hook secured to the movable member, said structure comprising an elongated flexible means connected to the hook and the fetus.

68. An apparatus for assisting a bovine animal to give birth to a calf comprising: an elongated linear supporting member, a spanner located adjacent one end of the supporting member adapted to engage the animal, means mounting a mid-portion of the spanner on the supporting member, said supporting member having an elongated series of detents formed therein, an elongated tubular member slidably and telescopically mounted on the supporting member, said tubular member having means adapted to accommodate structure attachable to the calf, and ratchet means on the movable member and engageable with said detents to move the tubular member with respect to the supporting member whereby the spanner will be moved into engagement with the animal and the movement of the tubular member will apply a pulling force on the structure attached to the calf and tubular member to assist the animal in giving birth to the calf.

69. The apparatus of claim 68 wherein: the spanner has a transverse middle section and forwardly directed end sections attached to the opposite ends of the middle section.

70. The apparatus of claim 68 wherein: the detents comprise holes in the supporting member.

71. The apparatus of claim 68 wherein: the ratchet means includes a handle, means pivotally mounting the handle on the tubular member, and tongue means operably connected to the handle and engageable with the detents on movements of the handle to move the tubular member relative to the supporting member.

72. The apparatus of claim 68 wherein: the ratchet means includes a handle, means pivotally mounting the handle on the tubular member, a first tongue connected to the handle and engageable with with the detents to move the tubular member in response to the movement of the handle, and a second tongue engageable with the detents to hold the tubular member and supporting member in fixed relative positions in one direction.

73. The apparatus of claim 72 including: means on the handle engageable with the second tongue to move and hold the second tongue in an operative position.

* * * * *

UNITED STATES PATENT AND TRADEMARK OFFICE

CERTIFICATE OF CORRECTION

PATENT NO. : 3,968,801

DATED : July 13, 1976

INVENTOR(S) : Jerry Lee Simon et al

It is certified that error appears in the above-identified patent and that said Letters Patent are hereby corrected as shown below:

Column 1, line 22, "requirers" should be --requires--.

Column 1, line 28, "prrovide" should be --provide--.

Column 3, line 39, "shafat" should be --shaft--.

Column 4, line 50, "shsorter" should be --shorter--.

Column 4, line 67, "whhereby" should be --whereby--.

Column 7, lines 5 and 6, "substanatially" should be --substantially--.

Column 7, line 10, "movemennts" should be --movements--.

Column 9, line 11, "direrction" should be --direction--.

Column 9, line 12, "forcce" should be --force--.

Column 9, line 41, "relase" should be --release--.

Column 10, Claim 10, after last line of last paragraph, two paragraphs were omitted:

--said handle, as it moves from said first to said second position, moving said release means out of engagement with sai locking means and moving said levering element into levering engagement with said supporting means,

UNITED STATES PATENT AND TRADEMARK OFFICE

CERTIFICATE OF CORRECTION

PATENT NO. : 3,968,801

DATED : July 13, 1976

INVENTOR(S) : Jerry Lee Simon et al (Page 2 of 2 pages)

It is certified that error appears in the above-identified patent and that said Letters Patent are hereby corrected as shown below:

continued movement of said handle towards said second position after said levering element is in levering engagement with said supporting means causing said movable means to move relative to said supporting means.--

Column 11, Claim 14, line 1, "mechhanism" should be --mechanism--

Column 15, line 46, "thhrough" should be --through--.

Column 19, line 4, after "means", insert --mounted--.

Column 20, line 17, "operative" should be --inoperative--.

Signed and Sealed this

Fifth Day of October 1976

[SEAL]

*Attest:*

RUTH C. MASON
*Attesting Officer*

C. MARSHALL DANN
*Commissioner of Patents and Trademarks*